United States Patent [19]

Jackson

[11] Patent Number: 4,459,110
[45] Date of Patent: Jul. 10, 1984

[54] DOWEL PIN LOCATOR ASSEMBLY AND METHOD OF MAKING POSITIVE DENTAL MODELS WITH REMOVABLE DIES

[76] Inventor: Robert M. Jackson, 308 S. Washington St., Clinton, Ky. 42031

[21] Appl. No.: 466,511

[22] Filed: Feb. 15, 1983

[51] Int. Cl.³ .............................................. A61C 19/00
[52] U.S. Cl. .................................................... 433/74
[58] Field of Search .................................. 433/74, 53

[56] References Cited
U.S. PATENT DOCUMENTS

| | | | |
|---|---|---|---|
| 2,842,845 | 7/1958 | Carlson | 433/74 |
| 3,277,576 | 10/1966 | Kraft | 433/53 |
| 3,469,316 | 9/1969 | Stern et al. | 433/74 |
| 3,478,428 | 11/1969 | Stengel | 433/74 |
| 3,702,027 | 11/1972 | Marshall et al. | 433/74 |
| 3,937,773 | 2/1976 | Huffman | 433/74 |
| 4,203,219 | 5/1980 | Wiener | 433/74 |
| 4,300,884 | 11/1981 | Camacho | 433/74 |

Primary Examiner—John J. Wilson
Attorney, Agent, or Firm—William R. Price

[57] ABSTRACT

A dowel pin locator assembly comprising a U-shaped base member having a race and anchoring members is placed so that the anchoring members are imbedded in the dental stone poured into the negative impression of a conventional impression tray. The race is left exposed, and after the dental stone has set, the positive model formed by the dental stone is separated from the negative impression. The race provides a snug fit with the head of a dowel pin, which is slideably positioned into the race so as to be in proper position for the ground-down tooth, requiring restoration. The head of the dowel pin cover is then bonded to the floor of the race and to the walls. The dowel pin projects upwardly through a slot in the race and is fitted with a dowel pin shank cover containing a central bore through which the shank projects. A full arch cover fits over the race member and the walls of the full race cover provides a snug fit for the dowel shank cover which is then locked into position by means of clips. Thereafter, the appropriate portions of the positive model are marked and the sections are sawed out through the slot portion of the U-shaped base member, so that the segment of the positive model and the U-shaped member containing the projecting shank can be removed and accurately relocated in the center of the model for the dental restoration work.

15 Claims, 13 Drawing Figures

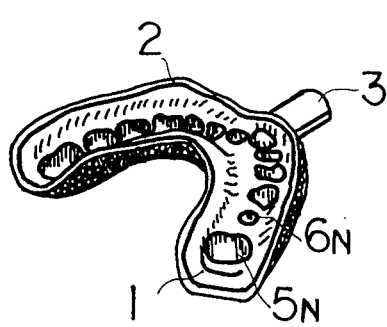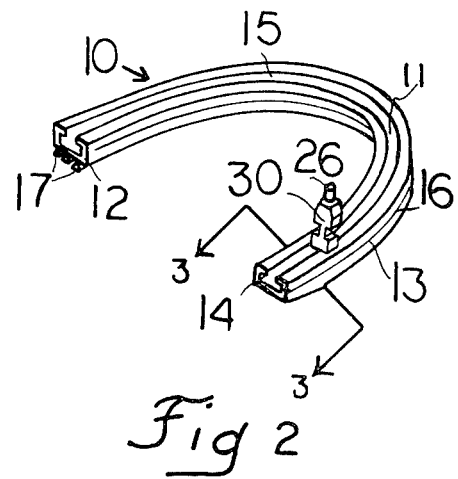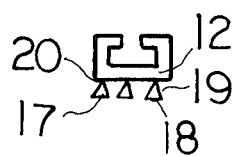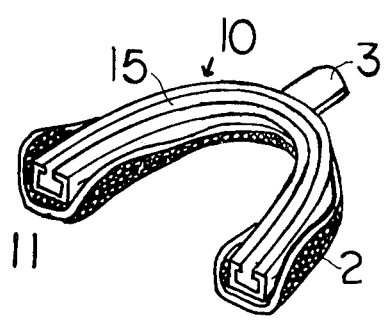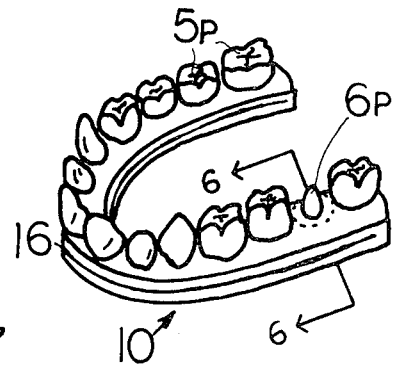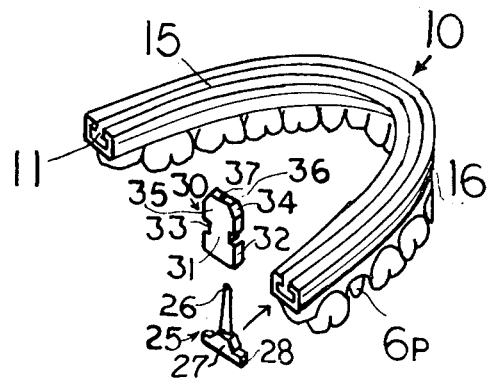

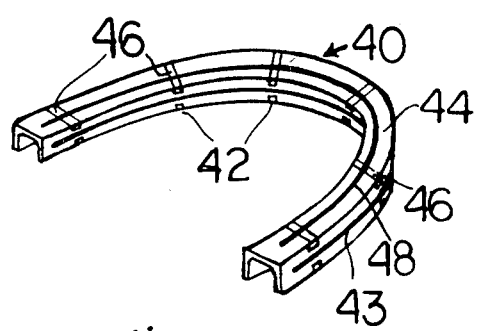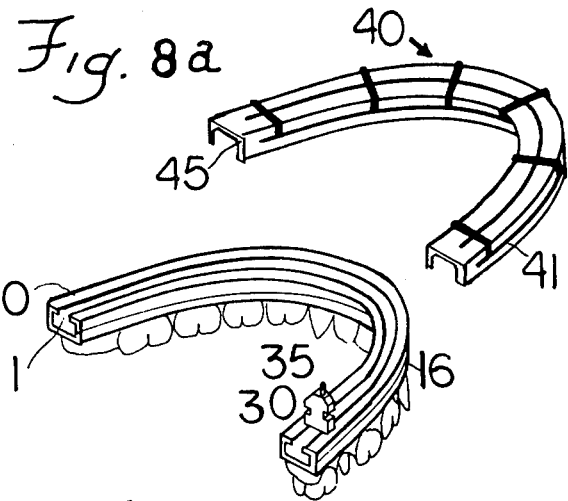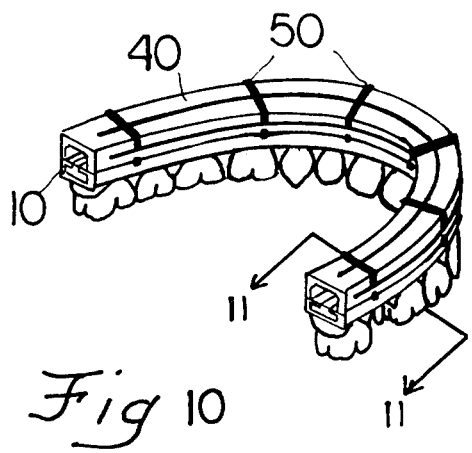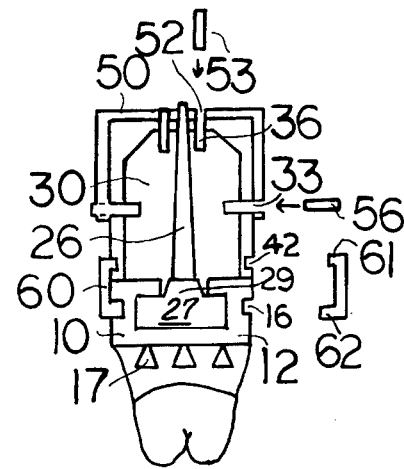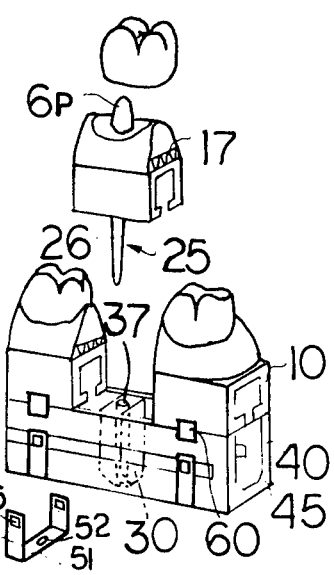

DOWEL PIN LOCATOR ASSEMBLY AND METHOD OF MAKING POSITIVE DENTAL MODELS WITH REMOVABLE DIES

FIELD OF THE INVENTION

The invention relates to an apparatus for preparing dental prosthesis, and more particularly for a dowel pin locator assembly for use in dental restoration work such as making brides, crowns, and the like, and to a process of making positive dental models from negative impressions with removable die sections.

SUMMARY OF THE PRIOR ART

To form the model of teeth which are to be prepared, it is usual practice to prepare a negative impression. After this is done, a dowel pin is placed substantially in the center of the negative impression of the particular teeth that require work. With the dowel pin in position, a first layer of die material is poured into the negative impression around the pin. After this die material has set up hard, a second layer is made by casting a base stone on top of the first. The base stone is usually made separable from the original impression of the teeth by a separation layer which consists of wax. The cast material is sawed in the area of the tooth or teeth requiring restoration and the tooth die or dies are simply lifted from the mold after first cutting the first die material with the saw from the adjacent die material. The die section is then removed simply by lifting the replica of the tooth. There is a problem in properly placing and aligning the die pins in the negative tooth impression. The methods previously used have been both tedious and time-consuming. It has been previously recognized, for example in U.S. Pat. No. 3,469,316, that there is a problem with properly positioning the dowel pin in the middle of the negative impression, or on an inclined axis. If the longitudinal axis of the dowel pin is located at a substantial angle relative to the vertical axis of the tooth impression, the bottom may be ruined when the tooth die is separated from the base stone. On the other hand, if the dowel extends into an adjacent tooth, the removal of a selected tooth die is extremely difficult, if not impossible.

It has also been previously proposed to provide a support over the dental impression in which a great many holes are drilled. Vertically disposed rods are slideably mounted in certain of these holes and the bottom end of each is used to support one of the pins. This device, however, requires a large base, making it difficult to vibrate the impression; which sometimes lossen while the stone is poured; causing the relationship of the pins to be lost. Additionally, a great amount of time is required in mounting the rods in the holes and setting the rods in the desired position.

Wiener, in U.S. Pat. No. 4,203,219, disclosed a U-shaped die locator made of a disposable plastic material which is placed into the unset dental stone, after having been poured into a negative dental impression to form a positive model. The Wiener die locator, however, has a second channel portion, which is imbedded within a suitable base material poured onto the model to form the base for the model. After the base material hardens, the model is separated from the base and the rib portion and the model are cut into model die, or sections, which are reseated on the rib portion of the base. This apparatus, however, requires a considerable amount of time for the setting of two sets of dental stone or base material, and does not provide for movable die pins for registry with the tooth or teeth requiring restoration.

SUMMARY OF THE INVENTION

A dowel pin locator assembly, comprising a U-shaped base member, having race and anchoring members, is provided for aligning dowel pin shanks in selected positions during a casting operation to produce a positive replica of a tooth or teeth from a negative impression formed in the impression material. The anchoring means of the U-shaped base member are set in the dental stone poured into the negative impression and are allowed to harden therein. The race member defines a channel in which the rectangular head of a dowel pin can be slidably positioned over one or more teeth or areas of the dental arch requiring restoration. Once the dowel pin is properly located, the head is bonded to the floor of the race with the shank portion extending upwardly through a slot therein for the provision of a dowel pin shank cover, having a centrally located bore adapted to fit over the shank. A full arch cover is then fit over the U-shaped base member and the dowel pin shank cover is secured and locked by means of clips to the full arch cover and the full arch cover is locked and secured by means of a second set of clips to the side walls of the U-shaped base member. Thereafter, the areas requiring restoration are marked and the segments are sawed into die sections comprising the nub or tooth to be supplied with a crown or the like. The die section includes the shank projecting from the race member. Since the dowel pin shank cover is locked into position in the full arch cover, the die section can be easily lifted from the positive model and replaced as required for the dental work.

BRIEF DESCRIPTION OF THE DRAWINGS

FIG. 1 is a perspective view of a full arch negative impression and a conventional impression tray.

FIG. 2 is a perspective view of a dowel pin locator in inverted position which illustrates a race defining a full arch for provision of a dowel pin having a dowel pin cover.

FIG. 3 is a sectional view taken along lines 3—3 illustrating the placement of the dowel pin head in the race of the dowel pin locator and illustrating triangular shaped anchors in depending position from the dowel pin locator.

FIG. 4 is a perspective view of the dowel pin locator set in the dental stone contained in the impression tray.

FIG. 5 is a perspective view of the positive dental model and dowel pin locator in upright position after separation from the negative impression and from the impression tray.

FIG. 6 is a sectional view taken along line 6—6 illustrating the relationship of the dowel pin locator to the positive dental model and illustrating the triangular anchors of the dowel pin locator set in dental stone.

FIG. 7 is a perspective view of the inverted positive dental stone model and the dowel pin locator illustrating the dowel pin and the dowel pin cover in position for insertion into the race of the dowel pin locator.

FIGS. 8&8a are perspective views of a full arch cover for use with the dowel pin locator.

FIG. 9 is a perspective view of the inverted dental stone model and dowel pin locator with the dowel pin and dowel pin cover mounted over the nub of the tooth prepared for reception of a crown.

FIG. 10 illustrates the positive dental stone model and the dowel pin locator set in dental stone forming the model and the relationship of the full arch cover mounted thereon and held in position by upper and lower clips.

FIG. 11 is a sectional view taken along lines 11—11, illustrating the relationship of the upper clip in engagement with the full arch cover and the dowel pin cover and the relationship of the lower clip in engagement with the full arch cover and the dowel pin locator.

FIG. 12 illustrates a segment of the dowel pin locator and the positive dental stone model in upright position after the model representing the nub of the ground down tooth has been sawed along the saw lines through the race of the dowel pin locator and further illustrating the finished crown adapted for placement on the nub of the positive dental stone model.

DESCRIPTION OF THE PREFERRED EMBODIMENT

Before describing the apparatus, some background information should be provided to assist in a complete understanding of the invention. The dowel pins described herein are routinely used in the dental office or dental laboratory to accurately maintain the position of a prepared tooth with adjacent dentition to provide for removing a die section during the construction of the prosthesis. The dowel pin position accurately positions the dowel pin in the center of the negative impression of the tooth, i.e., in axial alignment therewith, so that the prepared crown abutment impression (after saw cuts are made) makes die removal possible after the cast is completed. Proper alignment of the pin is necessary since placement of the pin other than at the center of the tooth impression, i.e., in the interproximal area, makes removal of the die difficult or impossible. Removal of the die from the master cast, or positive model, makes possible a margin determination, i.e., ditching and finer waxing of the restoration. The ability to place cast, or positive model, makes possible a margin determination, i.e., ditching and finer waxing of the restoration. The ability to place the die section back into the positive model in its relationship is critical for the proper fit of the finished prosthesis.

In the present invention, special dowel pins with specially adapted dowel pin heads and dowel pin shank covers are used to support the die sections in the proper position. Referring to the drawings in detail, a negative impression 1 fabricated of conventional impression material, such as hydro-colloid, rubber base polyether, or zinc-eugenol materials, is shown in a conventional impression tray 2 having a handle 3. The negative impressions of the various teeth are designated by the numeral 5N, whereas the negative impression of the ground-down tooth or nub in preparation for the crown is designated by 6N. The U-shaped base member 10 of the dowel pin locator assembly 9 is shown in FIG. 2 and consists of a race or track 11 having a floor 12 and side walls 13, terminating at the top by horizontally disposed flanges 14 which define a centrally located slot 15. A groove 16, located in the exterior surface of the side walls 13 of race 11, provides for an engagement with a clip, which will be described hereinafter. Projecting from the bottom of the exterior surface of floor 12 are a series of anchors 17 in triangular form, in which the apex 20 of the triangle joins the floor 12 of the U-shaped base member and the walls 19 of the triangle move diagonally towards the base 18. The dowel pin 25 is specially designed, having a shank portion 26 and a head portion 27, which terminates at each side in a straight vertical portion 28 for a snug fit with the interior side walls 13 of race 11. An upwardly projecting neck portion 29 surrounds the shank 26 for a slideable fit into slot 15. The shank cover 30 has two flat faces 31 and vertical side walls 32, containing a grooved portion 33 and a tapered end portion 34 for a snug fit within the channel of the full arch cover, which will be hereinafter described. The dowel pin shank cover 30 has a flat top portion 35 which in one embodiment shown in FIG. 11 has two laterally disposed detents 36 and a centrally located bore 37 for provision of the shank 26.

Referring now to FIG. 8, a full arch cover 40 of identical configuration to the U-shaped base member 10 is provided, and consists of side walls 41, having an identation 42 at the bottom of the side wall for a clip which will be hereinafter described. A slot 43 is located near the center of the side walls 41 and runs around the interior and exterior walls, forming the U-shaped arch. A roof 44 is formed with tapered corners 45, which are adapted for snug registry with the tapered end 34 of the dowel shank cover 30. There are transverse grooves 46 in the roof for the clip. The central groove 48, located on the inside of roof 44, provides a locking engagement with the top of shank 26.

Another embodiment of this invention is illustrated in the upper clip 50, which can be best seen in FIG. 11, has a roof portion 51 and an opening 52 for provision of locking pin 53, which fits in indentations 36 in the flat top portion 35 of the dowel pin shank cover 36. The lower clip 60 has an upper locking leg 61 which fits in the indentation 42 at the bottom of the side wall 41 of the full arch cover and a lower locking leg 62 fitting into the groove 16 in side wall 13 of the U-shaped base member.

As has previously been stated, it is essential in dental prosthetic work to position the dowel pin shank axially with the center portion of the tooth for which the prosthesis is being made. Thus, as is shown in FIG. 7, the head portion 27 of the dowel pin is adapted to slideably fit in the race 11 of the U-shaped base member. As is shown in FIG. 9, the dowel pin has been located axially with the positive model 6P of the nub for which a crown is to be made. Once this has been accomplished, the head is bonded into position by means of a heating device whereby the head is actually welded to the floor 12 of the U-shaped member 10, or by a cyanoacrylate glue, artfully placed so as to bond the head 27 with the race 11 and the straight vertical postion 28 with the side walls 13 of the U-shaped member 10. The neck portion 29 of the dowel pin head 27 extends through slot 15 of the U-shaped base member 10. The pin is adapted for provision of the dowel pin shank cover 30. A centrally located bore 37 snugly fits over the shank 26 of the dowel pin. Once the dowel pin is properly located with the head bonded into position in the race, axially aligned with the nub or ground-down tooth for which the restoration has been ordered, the full arch cover is placed over the U-shaped base member 10 and the upper clip 50 is arranged so that the roof portion of the upper clip projects transversely across the roof 44 of the full arch cover. If the locking pins are used, the locking pins 53 are positioned through holes 52 and into the groove 36 on the flat top portion of the dowel pin shank cover 30. Similarly, if locking pins are used with the clip, the pins 56 can slide through hole 55 of side wall 54 and into side detent means in the form of groove 33.

Thus, the dowel pin shank cover is firmly and stably connected to the full arch cover, both at the top and at the side. The full arch cover contains indentations 42 at the bottom of the side walls and the upper leg 61 of the lower clip 60 engages with this indentation and with the lower locking leg 62 engages with the groove 16 in the side wall 13 of the U-shaped base member. Once this has been accomplished, the entire dowel pin locator assembly is turned upwardly with the positive dental model and the model is marked for the saw lines, in this case, in the space on either side of the ground down nub 6P. The tooth is then sawed along the lines and and the sawed-out die segment can be easily lifted so that the shank 26 of the dowel pin 25 can be easily located and placed back into the central bore 37 of the shank cover 30, positively locked into position by the upper clip 50.

By this, it is within the scope of this invention to utilize a spring clip rather than a clip with locking pins, and in this case, the upper and lower legs are pulled aside out of position with the grooves located in the side walls and top walls of the top portions of the dowel pin shank cover 30. Similarly, the lower clip 60 can be a spring type clip so as to release the full arch cover from the U-shaped base member.

As previously indicated, once the die segment is in position to be removed and reset into the positive model, the dentist can make the proper steps to insure proper marginal fit of the crown or other prosthesis through fine waxing and ditching techniques to make the proper marginal determinations, etc. Once the die section is replaced in the master mold, the dentist can make certain that the prosthesis perfectly fits onto the nub or ground-down tooth and that the cusp of the teeth are in proper articulation with the remaining teeth.

While the invention in this case has been illustrated for the preparation of a crown, it is well within the scope of the art to utilize the apparatus for the restoration of several teeth in the form of bridgework, or even in the preparation of full sets of dental prostheses.

Many modifications will occur to those skilled in the art from the detailed description hereinabove given, which is meant to be examplary in nature and nonlimiting except so as to be commensurate in scope with the appended claims.

I claim:

1. A dowel pin locator assembly for use in dental restoration work, which comprises:
    A. a U-shaped base member, having:
        1. a race, and
        2. anchoring members;
    B. a dowel pin member having shank and head portions,
        1. said head portion having projecting sides slideably fitting in said race, and
        2. a dowel pin shank cover, having a central bore slideably fitting over said shank portion;
    C. a full arch cover, corresponding in configuration to said base member and having side walls and a roof which define a channel of a shape corresponding to said dowel pin shank cover snugly receiving said dowel pin shank cover therein;
    D. locking means for locking said full arch cover and said dowel pin shank cover together; and
    E. locking means for locking said full arch cover and said U-shaped base member together.

2. A dowel pin locator assembly, as defined in claim 1, in which said race comprises:
    A. a floor;
    B. vertically projecting side walls;
    C. inwardly projecting horizontal flanges; and
    D. a slot defined by the inwardly projecting horizontal flanges.

3. A dowel pin locator assembly, as defined in claim 2, in which the projecting sides of the head portion of said dowel pin terminate in straight vertically extending ends for snug fit with the vertically projecting side walls of said race.

4. A dowel pin locator assembly, as defined in claim 2, in which the head portion of said dowel pin projects upwardly in the form of a neck portion for a slideable fit in said slot.

5. A dowel pin locator assembly, as defined in claim 2, in which the vertically extending side walls of said race member contain a locking groove for engagement with the second locking means.

6. A dowel pin locator assembly, as defined in claim 1, in which the anchoring means are in the form of triangles, the apex of the triangle forming a junction with the floor of said base member and the side walls projecting diagonally toward the base of said triangle.

7. A dowel pin locator assembly, as defined in claim 1, in which said dowel pin shank cover contains detent grooves on each side for engagement with said first locking means.

8. A dowel pin locator assembly, as defined in claim 1, in which said dowel pin shank cover contains detent grooves in the top portion for engagement with said first locking means.

9. A dowel pin locator assembly, as defined in claim 1, in which the side walls of said cover contain a slot for engagement of one leg of said first locking means.

10. A dowel pin locator assembly, as defined in claim 1, in which said roof of said full arch cover contains a slot for provision of the locking member of said first locking means with said dowel pin shank cover.

11. A dowel pin locator, as defined in claim 1, in which the interior of said roof of said full arch cover has a centrally located groove for engagement with the end of said dowel pin shank.

12. A dowel pin locator assembly, as defined in claim 1, in which the lower side wall of said full arch cover contains detent portions for engagement with the locking member of said second locking means.

13. A method of making a positive dental model with removable die sections from a negative dental impression, which comprises the steps of:
    A. pouring dental stone into said negative impression;
    B. placing a U-shaped base member having a race and anchoring members in said dental stone and embedding said anchoring members in said dental stone before it sets;
    C. allowing said dental stone to set;
    D. separating said dental stone positive and U-shaped member embedded therein from said negative impression;
    E. inserting a dowel pin into said race into proper position relative to the tooth of the positive mold requiring restoration;
    F. bonding the dental dowel pin head to the floor of said race;
    G. placing a dowel pin shank cover over the shank of said dowel pin;
    H. placing a full arch cover over said race;
    I. locking said full arch cover to said dowel pin shank cover;

J. locking said full arch cover to said U-shaped base member;

K. sawing the positive model along the lines required for the restoration work to form a separate die or dies;

L. removing the die section, including the dowel pin, dowel pin shank and sawed out race portion of said U-shaped base member, from said positive model;

M. resetting the die section and dowel pin back into the positive model as required for restoration work.

14. A method of making a positive dental model assembly, as defined in claim 13, the improvement in sawing the positive model, which involves sawing the positive model through the dental stone portion and down through the top of the race portion of said U-shaped base member, but stopping short of sawing through the full arch cover.

15. A method of making a positive dental model assembly, as defined in claim 14, in which the sawed-out section provides a die member, including the shank portion of the dowel pin, but in which the bonded dowel pin shank cover remains in the full arch cover so that the die section can be fitted back over the dowel pin cover and the shank of the dowel pin inserted in the dowel pin shank cover.

* * * * *